(12) United States Patent
Auerbach

(10) Patent No.: US 10,227,161 B2
(45) Date of Patent: Mar. 12, 2019

(54) CARRIER RACK FOR PHARMACEUTICAL CONTAINERS

(71) Applicant: Schott Schweiz AG, St. Gallen (CH)

(72) Inventor: Judith Auerbach, Niederteufen (CH)

(73) Assignee: Schott Schweiz AG, St. Gallen (CH)

( * ) Notice: Subject to any disclaimer, the term of this patent is extended or adjusted under 35 U.S.C. 154(b) by 30 days.

(21) Appl. No.: 15/417,707

(22) Filed: Jan. 27, 2017

(65) Prior Publication Data

US 2017/0217637 A1   Aug. 3, 2017

(30) Foreign Application Priority Data

Jan. 28, 2016   (DE) .................. 10 2016 201 268
Jan. 9, 2017   (EP) ..................... 17150609

(51) Int. Cl.
| | |
|---|---|
| B65D 25/10 | (2006.01) |
| A61M 5/00 | (2006.01) |
| B65D 69/00 | (2006.01) |
| B01L 9/06 | (2006.01) |

(52) U.S. Cl.
CPC .......... B65D 25/108 (2013.01); A61M 5/002 (2013.01); A61M 5/008 (2013.01); B65D 69/00 (2013.01); B01L 9/06 (2013.01)

(58) Field of Classification Search
CPC .... A61M 5/008; A61M 5/002; A61M 5/3202; A61M 2005/3139; B65D 25/108
USPC ...................................................... 206/366
See application file for complete search history.

(56) References Cited

U.S. PATENT DOCUMENTS

| | | | |
|---|---|---|---|
| 3,643,812 A | | 2/1972 | Mander et al. |
| 4,919,264 A | * | 4/1990 | Shinall ............... A61M 5/3205 206/210 |
| 5,080,232 A | | 1/1992 | Leoncavallo et al. |
| 8,100,263 B2 | * | 1/2012 | Vanderbush ......... A61M 5/002 206/366 |
| 9,139,350 B2 | * | 9/2015 | Yeager ................... B65D 81/20 |
| 9,850,010 B2 | * | 12/2017 | Liversidge ............. A61B 50/20 |
| 2001/0052476 A1 | | 12/2001 | Heinz et al. |

(Continued)

FOREIGN PATENT DOCUMENTS

| | | |
|---|---|---|
| EP | 1 449 551 A1 | 8/2004 |
| EP | 2 119 436 A1 | 11/2009 |

(Continued)

OTHER PUBLICATIONS

Extended European Search Report dated Jun. 29, 2017 for European Patent Application No. 17 15 0609 (4 pages).

*Primary Examiner* — Shawn M Braden
(74) *Attorney, Agent, or Firm* — Taylor IP, P.C.

(57) ABSTRACT

A carrier rack for pharmaceutical containers or medical packaging products having a non-cylindrical symmetric flange. The carrier rack includes a plurality of through-openings defined by the carrier rack for accommodating the pharmaceutical containers or medical packaging products, and at least one member protruding above a top side of the carrier rack and having a height. Each member includes at least one of at least one bevel and at least one radius, wherein the at least one member is allocated to each one of the plurality of through-openings, and wherein at least one of the at least one bevel and the at least one radius interact with the non-cylindrical symmetric flange in such a way that the pharmaceutical containers or medical packaging products are aligned.

19 Claims, 4 Drawing Sheets

(56) References Cited

U.S. PATENT DOCUMENTS

| | | |
|---|---|---|
| 2009/0100802 A1 | 4/2009 | Bush et al. |
| 2010/0059461 A1 | 3/2010 | Landsberger et al. |
| 2012/0193256 A1* | 8/2012 | Gagnieux ............. A61M 5/008 206/366 |
| 2013/0186793 A1* | 7/2013 | Gagnieux ............. A61M 5/002 206/364 |
| 2015/0041349 A1 | 2/2015 | Liversidge |
| 2016/0206806 A1* | 7/2016 | Wright ................. A61M 5/002 |

FOREIGN PATENT DOCUMENTS

| | | |
|---|---|---|
| WO | 2011/000606 A1 | 1/2011 |
| WO | 2011/007194 A1 | 1/2011 |
| WO | 2012/126582 A1 | 9/2012 |

* cited by examiner

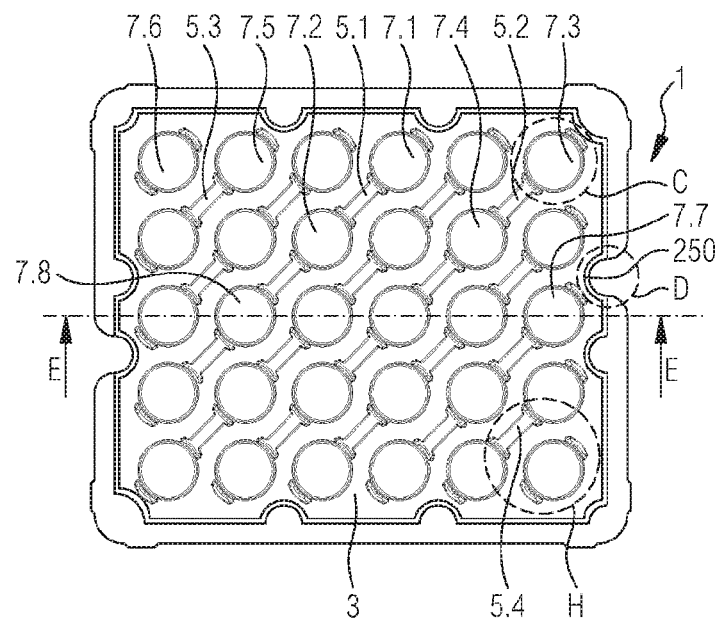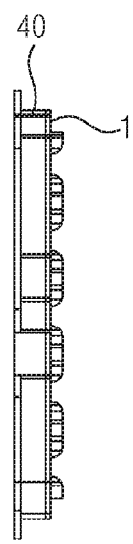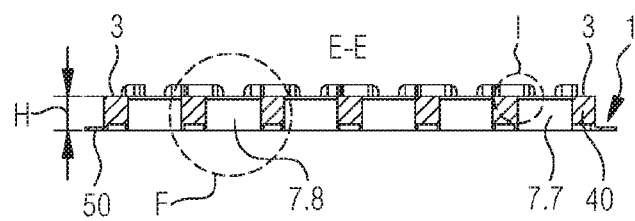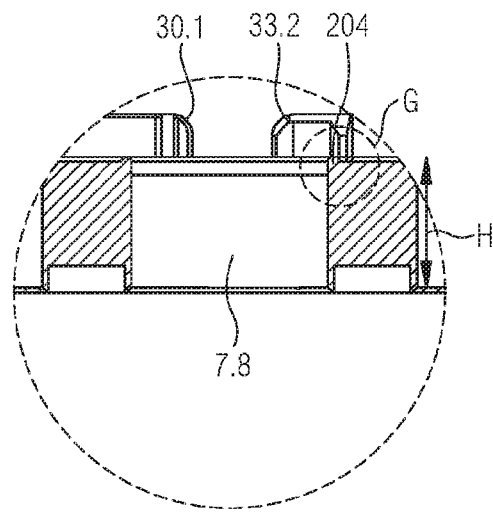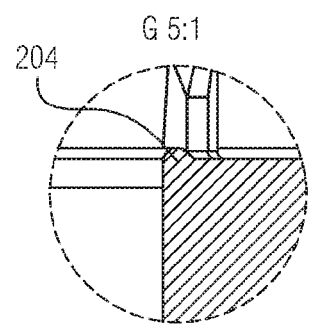

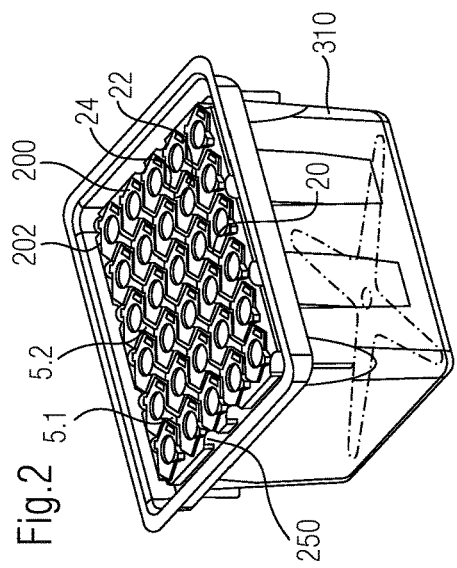
Fig.2
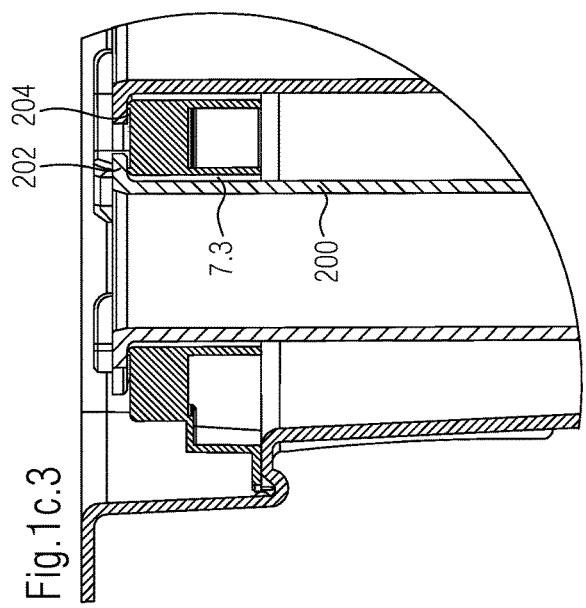
Fig.1c.3
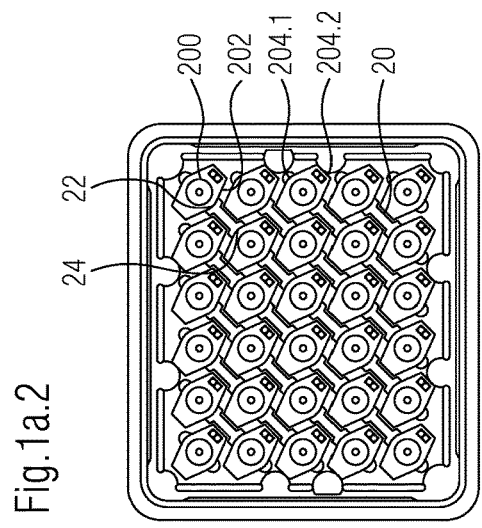
Fig.1a.2

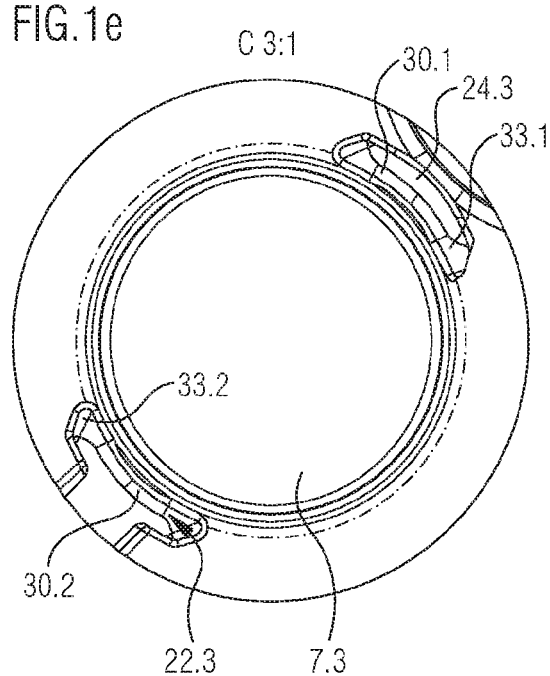
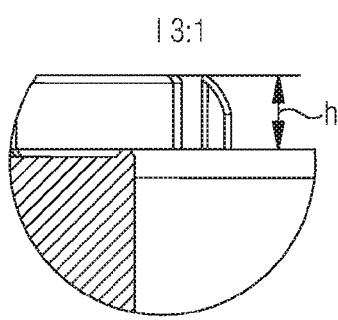
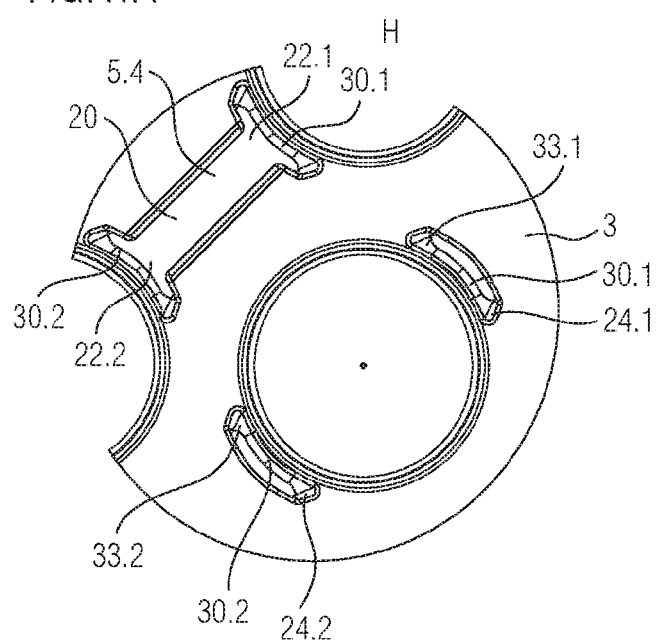
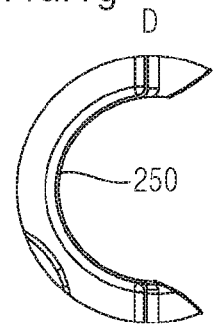

Fig.1f.2
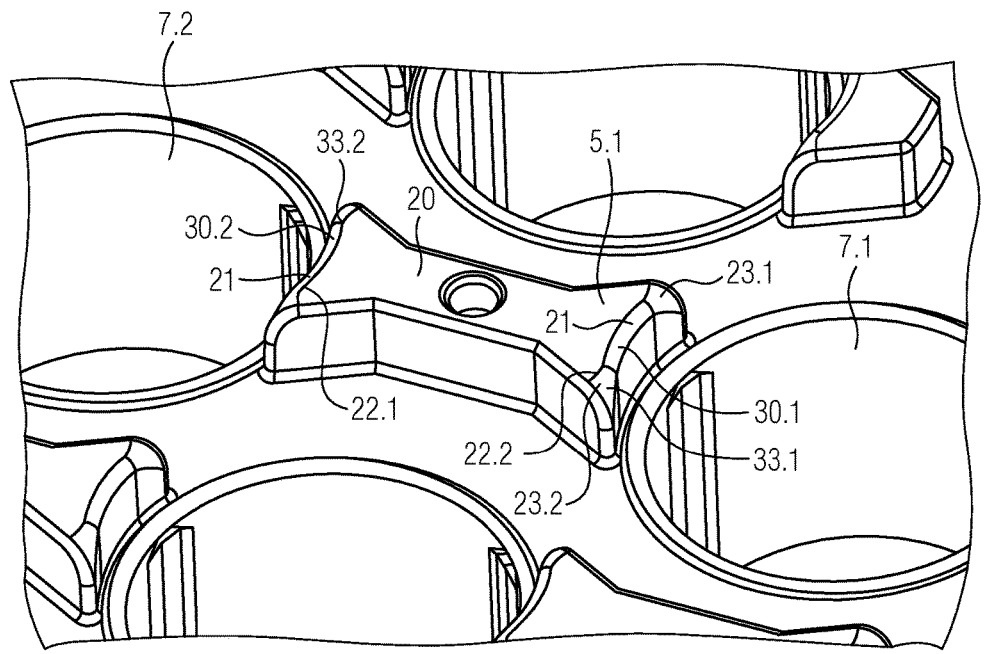
Fig.1f.3
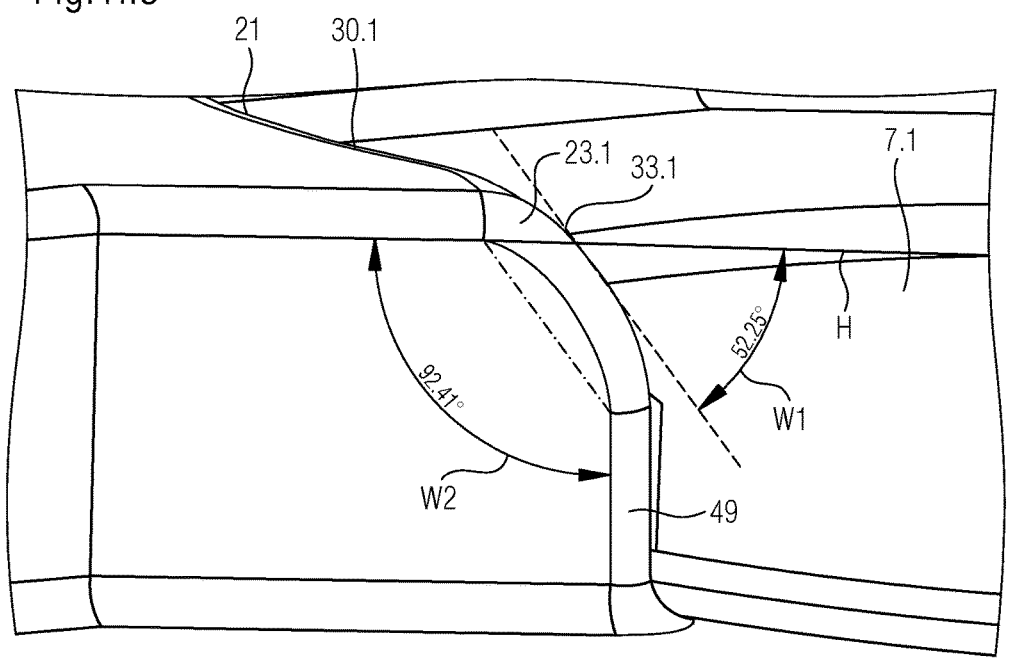

CARRIER RACK FOR PHARMACEUTICAL CONTAINERS

BACKGROUND OF THE INVENTION

1. Field of the Invention

The present invention relates to a carrier rack for pharmaceutical containers or medical packaging products, for example syringes, vials or cartridges, and more particularly to a carrier rack including through-openings to accommodate pharmaceutical containers or medical packaging products. The carrier rack moreover includes raised sections.

The present invention further relates to a transport and/or storage device for pharmaceutical containers or medical packaging products.

2. Description of the Related Art

For effective production of pharmaceutical containers or medical packaging products, for example syringes, vials or cartridges: these are preassembled in predefined configurations—so called nests—and are held defined in their position relative to each other, and are thereby subjected together and/or simultaneously to the respectively required production processes. The transport and storage of the pharmaceutical containers or medical packaging products to/from the devices performing the individual production processes, as well as positioning within these devices also occurs in these predefined configurations. For this purpose the pharmaceutical containers or medical packaging products are held and stored in a receptacle in the embodiment of a carrier rack, in a defined position relative to each other and relative to the carrier rack. This ensures simultaneous production of a high number of such pharmaceutical containers or medical packaging products in one single process step. The pharmaceutical containers or medical packaging products are individually suspended in receiving openings, for example in through-openings in carrier racks, are anchored or otherwise positioned therein, in order to protect the containers or packaging from damage during transport, and to ensure simultaneous further processing of the entire container arrangement. Such predefined arrangements with central control over the individual containers in the respective through-openings serve to simplify the collective further processing of the arrangement in predefined process steps, for example sterilization of the containers, filling of the containers, a collective safe transport to and from the respective processing devices, closing of the containers, etc. Collective further processing of such an arrangement, for example filling and closing of the pharmaceutical containers or packaging may for example occur in a device as described in WO 2011/000606 A1, wherein the arrangement of the pharmaceutical containers is subjected to the individual process steps held in place by a carrier rack. Such carrier racks comprise a receiving region that has a plurality of through-openings to accommodate pharmaceutical containers or medical packaging products, a defined handling region for holding the carrier rack and/or storage of the same. Generally, the carrier rack is manufactured out of plastic. The carrier rack with the pharmaceutical containers or packaging products positioned and centered therein is subjected to a multitude of stresses during the aforementioned production and transportation processes which can lead to undesirable deformations of the carrier rack, and which can considerably impair handling of the carrier rack, as well as the quality of the production processes. Various transport and/or storage devices for pharmaceutical containers or medical packaging products, for example syringes, vials or cartridges, wherein numerous pharmaceutical containers can be stored in a predefined position are also known from US 2009/100802 A1, EP 2119436 A1, WO 2011/007194 A1 and U.S. Pat. No. 3,643,812 A. An additional problem in the state of the art is that, during transport or even in the filling line, due to additional handling of the carrier rack with the inserted pharmaceutical containers or medical packaging products, these pharmaceutical containers could twist. In such a case the individual pharmaceutical containers or medical packaging products are no longer aligned and in part are even on top of one another. This occurs especially if the pharmaceutical containers or medical packaging products move in an axial direction, resulting in twisting. To avoid twisting, WO 2012/126582 describes a carrier rack with anti-twist devices in the embodiment of webs that include stop segments for a syringe collar and against which the syringe collars of the pharmaceutical containers fit. However, it is not known from WO 2012/126582 how an axial movement of the containers that subsequently can lead to twisting, can be prevented. Moreover, it is not known from WO 2012/126582 how, following an axial movement of the pharmaceutical containers, they can again be inserted into the opening.

An axial movement is avoided, for example through use of an additional plate, as described in US 20130186793 A1, or through protrusions as shown in EP 1 449 551 B1.

From US 2010/0059461 A1 a carrier rack for pharmaceutical products has become known, wherein the pharmaceutical products are inserted into openings in the carrier rack and are held in place by means of a raised section. US 2010/0059461 A1 does not show any raised sections with bevels or radii that interact with the flange of the packaging products to align the packaging products. The raised sections known from US 2010/0059461 A1 moreover serve to secure the packaging products, but not to align them. U.S. Pat. No. 5,080,232 also shows a carrier rack with openings into which pharmaceutical containers can be inserted. The openings are equipped with retainers to hold the inserted pharmaceutical containers in place. Alignment or insertion of the pharmaceutical products is not described in U.S. Pat. No. 5,080,232.

What is needed in the art is a carrier rack wherein the pharmaceutical containers or medical packaging products with at least one non-symmetrical flange can be reinserted into the opening, even after having bounced out, that is after a movement in axial direction, and wherein a subsequent twisting of the pharmaceutical containers or medical packaging products is prevented.

SUMMARY OF THE INVENTION

The present invention provides a carrier rack for pharmaceutical containers or medical packaging products with a non-cylindrical symmetric flange or collar, for example syringes, vials or cartridges, that includes through-openings to accommodate pharmaceutical products as well as a raised section protruding above the top side of the carrier rack and/or with individual components having one height and at least one bevel and/or one radius, wherein at least one raised section and/or one component has at least one bevel and/or radius allocated to each of the through-openings. The bevel and/or radius interact with the non-cylindrical symmetric flange or collar in such a way that the pharmaceutical containers or medical packaging products are aligned.

Alignment is understood to mean that the bevels/radii facilitate insertion of pharmaceutical containers or medical packaging products into the carrier rack and allow for centering of the containers. The bevels/radii ensure that the pharmaceutical containers or medical packaging products do not twist or, if they do twist, that the pharmaceutical containers or medical packaging products are returned into the predefined position with the assistance of the bevels and/or radii. The bevels/radii also serve to return the pharmaceutical containers into the predefined position after a bounce.

The effect of an alignment of the pharmaceutical containers occurs only if the pharmaceutical containers were not inserted under too severe of a misalignment.

Moreover, no alignment occurs if the pharmaceutical containers were inserted precisely and correctly. Self-alignment of the pharmaceutical containers is can be observed with small angle deviations of angles >0° to approximately 20°.

In another embodiment, the raised section has a height, and the height of the raised section protruding above the top side of the carrier rack is at least 2 mm, for example 2 mm to 20 mm, and can be 4 mm to 10 mm.

Because of the raised section protruding above the top side of the carrier rack, the pharmaceutical container is secured by the axial height against bouncing out, at least always within the limits of the defined height of the raised section.

The height of at least 2 mm of the raised section and/or the individual components in conjunction with the bevels and/or radii, prevent twisting, for example also in the case of axial bouncing. In contrast to EP 1 449 551 B1 and US 20130186793 A1 no additional plates or protrusions are necessary for this. Due to the fact that twisting of the individual pharmaceutical containers can be prevented with this type of arrangement, damage to the filling needle caused by leaning of the pharmaceutical containers or medical packaging products is avoided. Moreover, the carrier rack can be securely removed from a transport and/or storage device for pharmaceutical containers or medical packaging products, for example by lifting. Moreover it is possible to position stoppers that are placed onto the respective pharmaceutical containers at the correct height, thus preventing axial movement. Axial movement can also be inhibited through relatively simple measures, so that provision of additional protrusions or an additional plate that would make placement, for example of the carrier rack into the transport and/or storage device, difficult is not necessary.

Another embodiment provides that the raised sections are bone-shaped, with a center section and two side segments. The bevels and/or radii prevent twisting of the inserted pharmaceutical containers, as previously described.

If the raised sections are bone-shaped, they have bevels or radii, at least in the region of the side segments. The bevels and/or radii moreover make insertion of pharmaceutical containers or medical packaging products easier, especially for example syringes, vials or cartridges. For pharmaceutical containers or medical packaging products having at least one non-symmetrical flange, for example a collar, the inlet bevels moreover facilitate self-centering, for example after bouncing, in other words after an axial movement. They also ensure self-centering when bouncing to above the height of the raised section or the individual component. This is even possible if the pharmaceutical containers are twisted by 15°.

The bevels and/or radii are formed at the side segments of the bone-shaped raised section. Alternative to the bone-shaped raised-sections, individual raised sections that possibly also have bevels and/or radii are also possible.

Two bevels can be allocated to each through-opening, either in the form of side segments on a bone-shaped raised section or on an individual component.

On greater axial bouncing heights, for example of more than 5 mm, a raised section of for example 5 mm could be bounced over, and bouncing out or twisting of the pharmaceutical container, for example the syringe, primarily a syringe with a collar can occur. The inlet bevels according to the invention will then ensure that automatic reinsertion into the standard position is attained through gentle lateral vibrating, wherein the self-centering effect is achieved also with skewed flanges with a rotation angle of up to 15°.

In another embodiment, the carrier rack embodies a box profile with a top side and a bottom side. A box profile of this type is shown for example in WO 2012/126582, which is hereby incorporated into the current application in its entirety.

The box profile provides high stability of the carrier rack, since with a box profile a high flexural rigidity and torsional stiffness is achieved at minimal additional material use.

The box profile can have a box profile height that is in the range of 5 to 50 mm, for example 10 to 30 mm between the top side and bottom side of the carrier rack. Box profiles designed in this manner can be stacked, for example with a stack height of 15 to 40 mm.

The carrier rack can include handling regions. The handling regions serve to handle the carrier rack and allow for example for the carrier rack to be removed from transport and/or storage devices for pharmaceutical containers.

The rigidity of the box profile can be increased if means to increase the rigidity are placed on the tension side of the carrier rack. For example, this can be connectable ribs that connect two adjacent through-openings. These ribs can be located in an individual box profile region.

In another embodiment the carrier rack has a bulge in the region of the through-opening, for example a circumferential bulge. Because of the bulge, including the circumferential bulge, the contact surface between the syringe and the carrier rack is reduced, because the syringe is supported only on the bulge. The bulge moreover makes it possible, to lift the inserted syringe—as the pharmaceutical container—by gripping it, from the carrier rack.

A carrier rack according to the present invention can be used in a transport and/or storage device for pharmaceutical containers, for example syringes, vials or cartridges. This includes a storage container that can accommodate the fully loaded carrier rack.

To prevent bouncing, a cover can be provided for the storage container. The cover can be a film, for example a sealing film. Additional functional elements, for example sealing devices may be provided. Due to the inventive design of the carrier rack the containers stored therein remain—during transport and storage, even over a longer time period—centered in the through-opening with defined alignment in regard to their position relative to each other. Damage of the containers that are stored in the through-openings can thus be avoided.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1a.1 is a top view of the carrier rack without inserted pharmaceutical containers according to the present invention;

FIG. 1a.2 is a top view onto an inventive carrier rack with inserted pharmaceutical containers according to the present invention;

FIG. 1b.1 is a sectional view along line E-E in FIG. 1a.1 of the carrier rack, from which the box profile can be seen;

FIG. 1b.2 is a side view of the carrier rack according to FIG. 1a.1, from which the box profile can be seen;

FIG. 1c.1 illustrates detail F from FIG. 1b.1, including a through-opening without an inserted pharmaceutical container;

FIG. 1c.2 illustrates detail G from FIG. 1c.1;

FIG. 1c.3 illustrates the through-opening with an inserted pharmaceutical container;

FIG. 1d illustrates detail I from FIG. 1b.1;

FIG. 1e illustrates detail C from FIG. 1a.1;

FIG. 1f.1 illustrates detail H from FIG. 1a.1;

FIG. 1f.2 is a detailed view of the bone-shaped raised section, located between the two openings;

FIG. 1f.3 illustrates radii 33.1 of the raised section;

FIG. 1g illustrates detail D from FIG. 1a.1; and

FIG. 2 is a perspective view of the carrier rack, inserted into a transport and/or storage device according to the present invention.

Corresponding reference characters indicate corresponding parts throughout the several views. The exemplification set out herein illustrates one embodiment of the invention, in one form, and such exemplification is not to be construed as limiting the scope of the invention in any manner.

DETAILED DESCRIPTION OF THE INVENTION

FIG. 1a.1 shows a top view onto a carrier rack according to the present invention, without inserted syringes for pharmaceutical containers or medical packaging products, with a non-cylindrical symmetric flange, for example a collar. Carrier rack 1 for pharmaceutical containers includes a top side 3, herein illustrated. The carrier rack 1 also includes individual through-openings 7.1, 7.2, 7.3, 7.4, 7.5, 7.6, 7.7, 7.8 defined by the carrier rack 1. Placed on the top side 3 of carrier rack 1 is at least one member that protrudes above the top side of the carrier rack and has a height. The at least one member includes at least one bevel 30.1, 30.2 and/or radius 33.1, 33.2 that can be arranged on the member. The at least one member is allocated to each of the through-openings 7.1, 7.2, 7.3, 7.4, 7.5, 7.6, 7.7, 7.8. In the present embodiment, the at least one member includes raised sections 5.1, 5.2, 5.3, 5.4 and/or individual components 24.1, 24.2, 24.3. The raised sections 5.1, 5.2, 5.3, 5.4 are arranged between individual through-openings 7.1, 7.2, 7.3, 7.4, 7.5, 7.6, 7.7, 7.8 of the carrier rack 1. Through-openings 7.7 and 7.8 are located on sectional line E-E in FIG. 1a.1 and are therefore also illustrated in FIGS. 1b.1, 1c.1 and 1c.2.

The raised sections 5.1, 5.2, 5.3, 5.4 have a height (FIG. 1d) h that can be in the range of 2 mm to 20 mm, for example 4 mm to 10 mm. The minimum height of 2 mm for the raised section or the individual component results from the height of the non-symmetrical flange or collar of the pharmaceutical container, which can be approximately 2 mm. The minimum height ensures that the bevels and/or radii can act upon the flange for centering, for example in the event of a bounce. The upper limit of 20 mm for the raised section results from the tare weight of the pharmaceutical container that then becomes so heavy that a bounce is no longer possible. As shown in the top view onto the surface of top side 3 of carrier rack 1 with individual raised sections 5.1, 5.2, 5.3, 5.4, a respective raised section 5.1, 5.2, 5.3, 5.4 is bone-shaped, as illustrated in detail in FIGS. 1f.1-1f.3. This means it comprises a center section 20 and two side segments 22.1 and 22.2. However, the bone-shaped design of the raised section is in no way obligatory. The height of the raised section is between 2 and 20 mm. The raised section moreover comprises bevels 30.1, 30.2 and radii 33.1, 33.2. Bevels 30.1, 30.2 and radii 33.1, 33.2 are incorporated in the region of side segments 22.1, 22.2 of bone-shaped raised section 5.1, 5.2, 5.3, 5.4. As shown in FIGS. 1f.1-1f.3, bevels 3-.1, 30.2 and radii 33.1, 33.2 are not only formed in side segments 22.1, 22.2 of the bone-shaped raised section 5.1, 5.2, 5.3, 5.4, but can also be part of individual components 24.1, 24.2 on top side 3 of carrier rack 1. Individual components 24.1, 24.2 are components that have bevels 30.1, 30.2 and radii 33.1, 33.2 analogous to the bevels and radii of side segments 22.1, 22.2 of the bone-shaped raised section 5.1, 5.2, 5.3, 5.4. Within the scope of the current invention, components 24.1, 24.2 are designed analogous to side segments 22.1, 22.2 of bone-shaped raised section 5.1, 5.2, 5.3, 5.4. Individual components 24.1, 24.2 with bevels 30.1, 30.2 and radii 33.1, 33.2 can be designed in the edge region of surface 3 where bone-shaped raised sections cannot be arranged due to space limitations. All illustrated raised sections have bevels and radii. In the illustrated embodiment, bevels and radii abut one another. The effect of the invention is however also realized, if only bevels or only radii are provided. Provision of bevels and/or radii achieves that, due to the incline or the radius, easy insertion of the pharmaceutical container is possible. Moreover, self-centering is possible, even with pharmaceutical containers with non-symmetrical flange, for example syringe barrels with a collar, that were inserted skewed by 15°. An additional advantage of bevels and/or radii is, that the pharmaceutical containers, for example syringes—even if they move in axial direction beyond the raised section, for example bounce out—are reinserted into the opening. Same components as in FIG. 1a.1 are identified with same reference numbers. The design of bevels 30.1, 30.2 and radii 33.1, 33.2 is shown in detail in FIGS. 1f.2 and 1f.3. The radii are rounded, but have a central angle relative to horizontal H. To provide for self-centering according to the invention it is advantageous, if the central angle relative to horizontal H is in the range of 40° to 60°, for example between 45° and 60°. To support self-centering it may moreover be provided that the bevels and/or radii do not lead into the opening and angles below 90° relative to horizontal H but at angles greater than 90°, for example in the range of 91° to 95°, for example 92° to 93°. Insertion of the syringes into the opening is supported by such a measure.

FIG. 1a.2 illustrates a view of carrier rack 1 with inserted pharmaceutical containers—in this case syringe barrels 200 with syringe collars 202. The syringe collar is a special form of a non-symmetrical flange. As can be seen in FIG. 1a.2, edges 204.1, 204.2 of syringe collar 202 correspond with side segments 22.1, 22.2 and central section 20 of bone-shaped raised section 5.1 without fitting against it under normal circumstances. The syringe collar is controlled by bevels 30.1, 30.2 and/or radii 33.1, 33.2 at the side segments of the raised section and is guided into the appropriate through-openings (not shown). Bevels 30.1, 30.2 serve to facilitate easier insertion of the pharmaceutical containers into the openings and ensure that, even after bouncing out in axial direction they can again be easily inserted into the through-opening.

FIG. 1b.1 is a view along sectional line E-E in FIG. 1a.1. Top side 3 of carrier rack 1, as well as box profile 40 of carrier rack 1 are clearly visible. Box profile 40 has a height H that can be in the range of 5 to 50 mm, for example 10 to 30 mm, or 15 to 20 mm. Height H describes the height of the box profile from top side 3 of the carrier rack to bottom side 50 of the same. Also clearly visible in FIG. 1b.1 are the through-openings, identified in FIG. 1a.1 for example with 7.1, 7.2, 7.3. Height H of at least 5 mm for the box profile ensures, that the box profile does not distort. A distortion is problematic, since clean insertion into the through-openings is then no longer ensured.

FIG. 1b.2 illustrates a side view of the box-shaped profile of carrier rack 1, wherein the through-openings are not illustrated.

Detail F from FIG. 1b.1 is illustrated in FIG. 1c.1. Through-opening 7.8 as well as bevel 30.1 and radius 33.2 are clearly recognizable.

Detail G from FIG. 1c.1 is illustrated in FIG. 1c.2. Same components are identified with same reference numbers. Clearly visible in FIG. 1c.1 and especially in FIG. 1c.2 is a bulge 204 on which the syringe collar (not illustrated) of a syringe barrel (not illustrated) is supported when inserted.

FIG. 1c.3 illustrates a through-opening 7.3 with an inserted pharmaceutical container; in this case a syringe with syringe barrel 200 and syringe collar 202. Clearly visible is also bulge 204 that can be designed circumferential on the top side of the carrier rack. Syringe collar 202 of the syringe is supported on bulge 204. The contact surface between the syringe and the carrier rack is reduced by bulge 204. Moreover, the thus supported syringe can be lifted from the carrier plate by grippers.

FIG. 1d illustrates detail 1 from FIG. 1b.1. Clearly visible are heights h, namely the heights of the raised section that are in the range of 2 mm to 20 mm, for example 4 mm to 10 mm. Height H of the box profile is shown in FIG. 1b.1 and is in the range of 10 mm to 50 mm, for example 10 mm to 30 mm, or 15 to 20 mm. In the illustrated embodiment height h is 5.5 mm, height H is 15.5 mm. Height h of the raised section prevents bouncing out in axial direction, if the height of the movement in axial direction is less than the height of the raised section.

FIG. 1e shows detail C from FIG. 1a.1. The through-opening 7.3 is shown at the edge of carrier rack 1. In the embodiment according to FIG. 1e, one bevel 30.1 and one radius 33.1 is provided by an individual component 24.3; the other bevel 30.2 and the other radius 33.2 are provided by side segment 22.3 of a bone-shaped raised section.

As is the case with all previously illustrated through-openings 7.1, 7.2, 7.3, 7.4, 7.5, 7.6, 7.7, 7.8, two bevels 30.1, 30.2, 31.1, 31.2 and radii 33.1, 33.2, 35.1, 35.2 are allocated to the through-opening.

FIG. 1f.1 shows detail H from FIG. 1a.1. Clearly visible are bevels 30.1, 30.2 at side segments 22.1, 22.2 of bone-shaped raised section 5.4 and on individual components 24.1, 24.2. Again, two bevels and/or radii can be allocated to each through-opening.

FIG. 1f.2 shows again the raised bone-shaped section in detail that, as in FIG. 1f.2 is identified with 5.1 in FIG. 1a.1. As is the case in FIG. 1a.1, the opening between which the bone-shaped raised section 5.1 is arranged is identified with 7.1 or 7.2. To support centering of pharmaceutical containers—for example those having a flange—that are inserted into openings 7.1, 7.2, bone-shaped raised section 5.1 has a center region 21 in the region of side segments 22.1, 22.2, opposite opening 7.1, 7.2. Moreover, two side segments 23.1, 23.2 respectively abut to center region 21. Center region 21 comprises a bevel 30.1, 30.2 and side segments 23.1, 231, radii 33.1, 33.2. As shown in detail in FIG. 1f.3, bevels 30.1, 30.2 and radii 33.1, 33.2 have a median angle W1 relative to a horizontal H, by which radius 33.1, 33.2 or bevel 30.1, 30.2 is tilted. Median angle W1 at which bevel 30.1, 30.2 is tilted is in the range of 40° to 65°, for example 45° to 60°. In the illustrated embodiment it is 52.25°. If angle W1 is selected in the specified range, self-centering of pharmaceutical containers that are inserted in opening 7.1 occurs, even if the containers—including those with a flange—are inserted into the opening at a slant or bounce out of the same. This is achieved in that the radii and/or bevels are tiled below an angle W1 relative to the horizontal and support alignment of the containers. As indicated in FIG. 1f.3, openings 7.1, 7.2 may not display a 90° angle relative to horizontal H, but instead angle W2 greater than 90°, for example in the range of 91° to 95°. The openings in lower section 49 are designed diagonally which again, supports alignment of containers that are inserted at an angle.

FIG. 1g illustrates detail D from FIG. 1a.1. FIG. 1g illustrates handling region 250 with which carrier rack 1 can be lifted for example from a container 310, as illustrated in FIG. 2.

FIG. 2 illustrates a multitude of pharmaceutical containers or medical packaging products having a non-symmetrical flange, for example a collar 202, inserted in an inventive carrier rack 1 which in turn is placed in a transport or storage device in the embodiment of a tub 310. Carrier rack 1, loaded with the pharmaceutical containers, in this case syringes 200 with collars 202 can be placed into the transport and storage device. Storage container 310 can be in the embodiment of a tub. The carrier rack can be suspended in the tub-like storage container 310. Storage of carrier rack 1 in the storage container can be realized through friction fit or form fit. As is clearly show in FIG. 2, a multitude of raised sections 5.1, 5.2 are provided on surface H of the carrier element that, at least in part are bone-shaped, in other words have a center section 20 and two side segments 22.1, 22.2. As can be clearly seen in FIG. 2, collar 202 corresponds with the respective pharmaceutical container with side surfaces 22.1, 22.2 of the raised sections without making contact with these under normal circumstances. Due to the design of the raised sections 5.1, 5.2 having a height h in the range of 2 mm to 20 mm, for example 4 mm to 10 mm, with bevels and/or radii, insertion of the syringes is supported. Moreover, during an axial movement of the syringes to above the height of the raised section, twisting of the containers and overlapping of the individual collars is largely prevented.

For transportation, the tub can be equipped with a cover, for example a film (not illustrated). In such a case, movement of the syringe in axial direction to above the raised section is completely prevented, because the syringes would be held down by the cover.

Moreover, a carrier rack is specified, that provides anti-twist protection, wherein the anti-twist protection prevents twisting during axial movement of the individual pharmaceutical containers that are inserted into the carrier rack.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A carrier rack for pharmaceutical containers or medical packaging products having a non-cylindrical symmetric flange, the carrier rack comprising:
   a plurality of through-openings defined by the carrier rack for accommodating the pharmaceutical containers or medical packaging products; and
   at least one member protruding above a top side of the carrier rack and having a height, each said member including at least one of at least one bevel and at least one radius, wherein said at least one member is allocated to each one of the plurality of through-openings, and wherein at least one of the at least one bevel and the at least one radius interact with the non-cylindrical symmetric flange in such a way that the pharmaceutical containers or medical packaging products are self-aligned at angle deviations from greater than 0° to 20° upon being inserted into the plurality of through-openings by at least one of said at least one bevel and said at least one radius and are held in place securely with an anti-twist protection.

2. The carrier rack according to claim 1, wherein said at least one member is at least one of:
   at least one raised section; and
   at least one individual component.

3. The carrier rack according to claim 1, wherein the at least one bevel and the at least one radius each include a median angle relative to a horizontal, the median angle is in the range of 40° to 65°.

4. The carrier rack according to claim 3, wherein said median angle is in the range of 45° to 60°.

5. The carrier rack according to claim 3, wherein said plurality of through-openings each have an angle greater than 90° relative to the horizontal.

6. The carrier rack according to claim 5, wherein said angle of said plurality of through-openings is in the range of 91° to 95° relative to the horizontal.

7. The carrier rack according to claim 1, wherein said carrier rack includes at least one of two bevels and two radii of said least one member, which are allocated to each through-opening.

8. The carrier rack according to claim 7, wherein at least one of said bevels and radii are arranged on said at least one member, said at least one member includes at least one of at least one individual component and at least one raised section, said at least one raised section includes at least one side segment such that said at least one of said bevels and radii are arranged on at least one of the at least one individual component and on said at least one side segment of the at least one raised section.

9. The carrier rack according to claim 1, wherein said height of said at least one member is at least 2 mm.

10. The carrier rack according to claim 2, wherein said at least one raised section includes a center section and two side segments.

11. The carrier rack according to claim 1, wherein the carrier rack has a box profile including a top side and a bottom side, and the box profile has a box profile height, which is in the range of 5 to 50 mm between the top side and the bottom side of the box profile of the carrier rack.

12. The carrier rack according to claim 11, wherein said box profile height is in the range of 10 to 30 mm.

13. The carrier rack according to claim 11, wherein the carrier rack is stacked, with a stack height of 14 mm to 40 mm.

14. The carrier rack according to claim 1, wherein the carrier rack further includes at least one handling region.

15. The carrier rack according to claim 1, wherein the carrier rack further includes a plurality of connectable ribs that increase rigidity of the carrier rack.

16. The carrier rack according to claim 1, wherein the carrier rack further includes a bulge in a region of the plurality of through-openings.

17. The carrier rack according to claim 1, wherein said non-cylindrical symmetric flange is a collar.

18. The carrier rack according to claim 1, wherein said pharmaceutical containers or medical packaging products include syringes, vials or cartridges.

19. A transport or storage device for pharmaceutical containers or medical packaging products, including syringes, vials, and cartridges having a non-symmetrical flange, said transport or storage device comprising:
   a carrier rack, including:
      a plurality of through-openings defined by the carrier rack for accommodating the pharmaceutical containers or medical packaging products; and
      at least one member protruding above a top side of the carrier rack and having a height, each said member including at least one of at least one bevel and at least one radius, wherein said at least one member is allocated to each one of the plurality of through-openings, and wherein at least one of the at least one bevel and the at least one radius interact with the non-symmetrical flange in such a way that the pharmaceutical containers or medical packaging products are self-aligned at angle deviations from greater than 0° to 20° upon being inserted into the plurality of through-openings by at least one of said at least one bevel and said at least one radius and are held in place securely with an anti-twist protection;
   a storage container that accommodates the carrier rack; and
   at least one cover that closes the storage container.

* * * * *